(12) United States Patent
Ng et al.

(10) Patent No.: US 9,745,528 B2
(45) Date of Patent: *Aug. 29, 2017

(54) RING OPENING CROSS METATHESIS OF VINYL TERMINATED POLYMERS AND THEIR FUNCTIONALIZED DERIVATIVES FOR FOULING MITIGATION IN HYDROCARBON REFINING PROCESSES

(71) Applicant: ExxonMobil Research and Engineering Company, Annandale, NJ (US)

(72) Inventors: Man Kit Ng, Basking Ridge, NJ (US); Glen B. Brons, Leland, NC (US); Matthew W. Holtcamp, Huffman, TX (US); Donna J. Crowther, Seabrook, TX (US); Patrick Brant, Seabrook, TX (US); Hong Cheng, Bridgewater, NJ (US); Clarence Chase, Bensalem, PA (US)

(73) Assignee: EXXONMOBIL RESEARCH AND ENGINEERING COMPANY, Annandale, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/131,461

(22) Filed: Apr. 18, 2016

(65) Prior Publication Data

US 2016/0264891 A1    Sep. 15, 2016

Related U.S. Application Data

(62) Division of application No. 13/804,907, filed on Mar. 14, 2013, now Pat. No. 9,334,460.

(51) Int. Cl.
*C10G 75/04* (2006.01)
*C10L 10/04* (2006.01)
(Continued)

(52) U.S. Cl.
CPC ........... *C10G 75/04* (2013.01); *C07D 209/52* (2013.01); *C08F 8/32* (2013.01); *C08F 210/06* (2013.01);
(Continued)

(58) Field of Classification Search
CPC ...................................................... C10G 75/04
(Continued)

(56) References Cited

U.S. PATENT DOCUMENTS 3,454,555 A   7/1969   van der Voort et al.
3,565,804 A   2/1971   Honnen et al.
(Continued)

FOREIGN PATENT DOCUMENTS

EP   355895 A2    2/1990
EP   0767182 A2   4/1997
(Continued)

OTHER PUBLICATIONS

Kropp et al., "Surface-Mediated Reactions. 1. Hydrohalogenation of Alkenes and Alkynes", Journal of the American Chemical Society, May 21, 1990, pp. 7433-7434, vol. 112 (20), ACS Publications.
(Continued)

*Primary Examiner* — Ellen McAvoy
(74) *Attorney, Agent, or Firm* — Glenn T. Barrett

(57) ABSTRACT

A compound useful for reducing fouling in a hydrocarbon refining process is provided. A method for preparing the compound includes functionalizing a polymer having a vinyl chain end to obtain a terminal group having one or more anhydride units, and reacting the anhydride units with a polyamine. Methods of using the compound and compositions thereof are also provided.

40 Claims, 3 Drawing Sheets

(51) Int. Cl.
*C07D 209/52* (2006.01)
*C08F 8/32* (2006.01)
*C10L 1/238* (2006.01)
*C08F 210/06* (2006.01)
*C08F 210/08* (2006.01)

(52) U.S. Cl.
CPC ............ *C08F 210/08* (2013.01); *C10L 1/238* (2013.01); *C10L 10/04* (2013.01)

(58) Field of Classification Search
USPC .................................................. 208/48 AA
See application file for complete search history.

(56) References Cited

U.S. PATENT DOCUMENTS

| | | | |
|---|---|---|---|
| 3,898,056 A | 8/1975 | Honnen | |
| 4,368,133 A | 1/1983 | Forsberg | |
| 4,489,194 A | 12/1984 | Hayashi | |
| 5,616,153 A | 4/1997 | Mike et al. | |
| 5,746,786 A | 5/1998 | Mueller et al. | |
| 5,777,041 A | 7/1998 | Emert et al. | |
| 6,017,859 A | 1/2000 | Rossi et al. | |
| 6,303,703 B1* | 10/2001 | Kinder | C08F 8/32 525/333.7 |
| 6,331,656 B1 | 12/2001 | Blankertz et al. | |
| 7,122,113 B2 | 10/2006 | Cornelisse | |
| 7,682,491 B2 | 3/2010 | Syrinek | |
| 8,063,232 B2 | 11/2011 | Hagadorn et al. | |
| 8,231,695 B2 | 7/2012 | Cunningham et al. | |
| 8,283,419 B2 | 10/2012 | Hagadorn et al. | |
| 8,372,930 B2 | 2/2013 | Brant et al. | |
| 8,399,725 B2 | 3/2013 | Brant et al. | |
| 8,951,409 B2 | 2/2015 | Ng et al. | |
| 9,334,460 B2* | 5/2016 | Ng | C10L 10/04 |
| 9,441,171 B2* | 9/2016 | Ng | C08F 8/32 |
| 2004/0152843 A1* | 8/2004 | Taguchi | C08G 61/06 525/328.8 |
| 2005/0261440 A1 | 11/2005 | Dickakian et al. | |
| 2006/0123696 A1 | 6/2006 | Gaughan et al. | |
| 2008/0223755 A1 | 9/2008 | Roy-Auberger et al. | |
| 2009/0318644 A1 | 12/2009 | Brant et al. | |
| 2009/0318646 A1 | 12/2009 | Brant et al. | |
| 2010/0038290 A1 | 2/2010 | Wang et al. | |
| 2010/0170829 A1* | 7/2010 | Ng | C10G 9/00 208/48 AA |
| 2011/0147275 A1 | 6/2011 | Ng et al. | |
| 2012/0245310 A1 | 9/2012 | Crowther et al. | |
| 2012/0245311 A1 | 9/2012 | Crowther et al. | |
| 2012/0245312 A1 | 9/2012 | Holtcamp et al. | |
| 2012/0245313 A1 | 9/2012 | Crowther et al. | |
| 2012/0309998 A1 | 12/2012 | Holtcamp et al. | |
| 2013/0008830 A1 | 1/2013 | Ng et al. | |
| 2014/0262953 A1 | 9/2014 | Ng et al. | |
| 2014/0275433 A1 | 9/2014 | Ng et al. | |
| 2014/0275663 A1 | 9/2014 | Brons | |
| 2016/0215068 A1* | 7/2016 | Edgar | A61K 47/38 |

FOREIGN PATENT DOCUMENTS

| | | |
|---|---|---|
| GB | 1507379 A | 4/1978 |
| GB | 2183243 A | 6/1987 |
| WO | 0063257 A1 | 10/2000 |
| WO | 02083747 A2 | 10/2002 |
| WO | 2007039083 A1 | 4/2007 |
| WO | 2008156806 A1 | 12/2008 |
| WO | 2013006353 A1 | 1/2013 |
| WO | 2014047531 A1 | 3/2014 |

OTHER PUBLICATIONS

Resconi et al., "Olefin Polymerization at Bis(pentamethylcyclopentadienyl)zirconium and -hafnium Centers: Chain-Transfer Mechanisms", Journal of the American Chemical Society, Jan. 1, 1992, pp. 1025-1032, vol. 114, iss. 3, ACS Publications.
PCT/US2014/017057 Search Report and Written Opinion dated Apr. 15, 2014.
Majchrzak et al., "An autonomous self-healing system based on ROMP of norbornene dicarboximide monomers", Polymer, Oct. 1, 2012, vol. 53, No. 23, Elsevier.
PCT/US2014/017063 International Search Report and Written Opinion dated May 9, 2014.
Stevens, "Polymer Chemistry an Introduction", 2nd ed., Oxford University Press, 1990, p. 19 and 82.
PCT/US2014/017067 International Search Report and Written Opinion dated May 9, 2014.
PCT/US2014/015990 International Search Report and Written Opinion dated Oct. 9, 2014.
PCT/US2014/015974 International Search Report and Written Opinion dated Jun. 27, 2014.

* cited by examiner

RING OPENING CROSS METATHESIS OF VINYL TERMINATED POLYMERS AND THEIR FUNCTIONALIZED DERIVATIVES FOR FOULING MITIGATION IN HYDROCARBON REFINING PROCESSES

CROSS-REFERENCE TO RELATED APPLICATIONS

This application is a divisional of U.S. patent application Ser. No. 13/804,907 filed on Mar. 14, 2013 and recently allowed, which itself relates to International Application PCT/US2012/059191, filed on Oct. 8, 2012, the disclosure of which is incorporated by reference in its entirety herein.

This application is related co-pending U.S. application, filed on the even date herewith, and identified by Ser. No. 15/131,557 also entitled "Ring Opening Cross Metathesis of Vinyl Terminated Polymers and Their Functionalized Derivatives for Fouling Mitigation in Hydrocarbon Refining Processes" and is hereby incorporated by reference herein in its entirety.

This application is also related to the following U.S. patent application Ser. No. 13/826,512 filed on Mar. 14, 2013; U.S. Ser. No. 13/826,059 filed on Mar. 14, 2013 and granted (U.S. Pat. No. 9,212,326) on Dec. 15, 2015; U.S. Ser. No. 13/804,727 filed on Mar. 14, 2013 and allowed Aug. 26, 2015; U.S. Ser. No. 13/804,507 filed on Mar. 14, 2013 and granted (U.S. Pat. No. 9,085,737) on Jul. 21, 2015; U.S. Ser. No. 14/711,144 filed on May 13, 2015; U.S. Ser. No. 14/870,665 filed on Sep. 30, 2015; U.S. Ser. No. 14/870,839 filed on Sep. 30, 2015; U.S. Ser. No. 14/935,978 filed on Nov. 9, 2015; U.S. Ser. No. 14/950,316 filed on Nov. 24, 2015; and U.S. Ser. No. 14/950,460 filed on Nov. 24, 2015, each of which is hereby incorporated in its entirety by reference herein.

TECHNICAL FIELD

The disclosed subject matter relates to additives to reduce fouling of crude hydrocarbon refinery components, and methods and systems using the same.

BACKGROUND

Petroleum refineries incur additional energy costs, perhaps billions per year, due to fouling and the resulting attendant inefficiencies caused by the fouling. More particularly, thermal processing of crude oils, blends and fractions in heat transfer equipment, such as heat exchangers, is hampered by the deposition of insoluble asphaltenes and other contaminants (i.e., particulates, salts, etc.) that may be found in crude oils. Further, the asphaltenes and other organics are known to thermally degrade to coke when exposed to high heater tube surface temperatures.

Fouling in heat exchangers receiving petroleum-type process streams can result from a number of mechanisms including chemical reactions, corrosion, deposit of existing insoluble impurities in the stream, and deposit of materials rendered insoluble by the temperature difference ($\Delta T$) between the process stream and the heat exchanger wall. For example, naturally-occurring asphaltenes can precipitate from the crude oil process stream, thermally degrade to form a coke and adhere to the hot surfaces. Further, the high $\Delta T$ found in heat transfer operations result in high surface or skin temperatures when the process stream is introduced to the heater tube surfaces, which contributes to the precipitation of insoluble particulates. Another common cause of fouling is attributable to the presence of salts, particulates and impurities (e.g., inorganic contaminants) found in the crude oil stream. For example, iron oxide/sulfide, calcium carbonate, silica, sodium chloride and calcium chloride have all been found to attach directly to the surface of a fouled heater rod and throughout the coke deposit. These solids promote and/or enable additional fouling of crude oils.

The buildup of insoluble deposits in heat transfer equipment creates an unwanted insulating effect and reduces the heat transfer efficiency. Fouling also reduces the cross-sectional area of process equipment, which decreases flow rates and desired pressure differentials to provide less than optimal operation. To overcome these disadvantages, heat transfer equipment are ordinarily taken offline and cleaned mechanically or chemically cleaned, resulting in lost production time.

There is a need to reduce precipitation/adherence of particulates and asphaltenes from the heated surface to prevent fouling, particularly before the asphaltenes are thermally degraded or coked. Such reduction will improve the performance of the heat transfer equipment, decrease or eliminate scheduled outages for fouling mitigation efforts, and reduce energy costs associated with the processing activity.

Antifoulant additives have been described in a number of commonly-owned applications, including U.S. Patent Application Publication Nos. 20110147275 and 20100170829, the disclosure of each of which is incorporated herein by reference in its entirety. However, there remains a need for alternative antifoulant additives capable of reducing precipitation and/or adherence of particulates and asphaltenes.

SUMMARY

In accordance with one aspect of the disclosed subject matter, a compound is provided. The compound being represented by

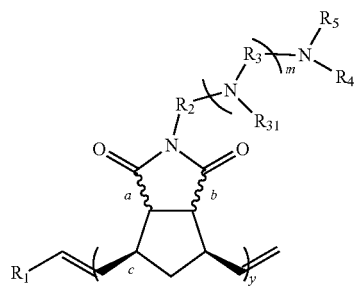

wherein $R_1$ is a branched or straight-chained $C_{10}$-$C_{800}$ alkyl or alkenyl group;

y is an integer between 1 to 20 inclusive;

m is an integer between 0 and 10 inclusive;

a and b are C—C bonds in cis-configuration with respect to each other and in either cis- or trans-configuration with respect to bond c;

$R_2$ and $R_3$ are each independently a $C_1$-$C_4$ branched or straight chained alkylene group;

$R_{31}$ is hydrogen or —$R_8$-$R_9$, wherein either (a) $R_8$ is $C_1$-$C_4$ branched or straight chained alkylene group, and $R_9$ is

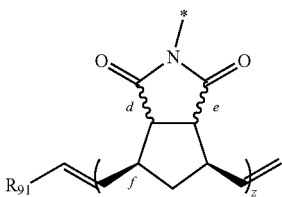

wherein $R_{91}$ is a branched or straight-chained $C_{10}$-$C_{800}$ alkyl or alkenyl group, the asterisk (*) indicates a connecting point with $R_8$, d and e are C—C bonds in cis-configuration with respect to each other and in either cis- or trans-configuration with respect to bond f, and z is an integer between 1 to 20 inclusive; or (b) $R_8$ and $R_9$ together are a $C_1$-$C_4$ branched or straight chained alkyl group optionally substituted with one or more amine groups; and wherein the —$N(R_{31})$—$R_3$— repeat unit is optionally interrupted in one or more places by a nitrogen-containing heterocyclic cycloalkyl group; and wherein $R_4$ and $R_5$ are each independently selected from (a) hydrogen, (b) —$R_6$-$R_7$, wherein $R_6$ is $C_1$-$C_4$ branched or straight chained alkylene group, and $R_7$ is

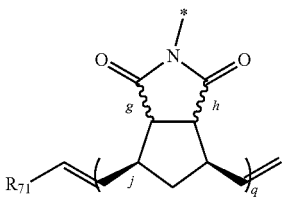

wherein $R_{71}$ is a branched or straight-chained $C_{10}$-$C_{800}$ alkyl or alkenyl group, the asterisk (*) indicates a connecting point with $R_6$, g and h are C—C bonds in cis-configuration with respect to each other and in either cis- or trans-configuration with respect to bond j, and q is an integer between 1 to 20 inclusive; or (c) a bond connected to $R_{31}$ in the m-th —$N(R_{31})$—$R_3$— repeat unit.

According to another aspect of the disclosed subject matter, a method for preparing a compound is provided. The method includes:

(a) converting a polymer base unit $R_{11}$, which is a branched or straight-chained $C_{10}$-$C_{800}$ alkyl or alkenyl group having a vinyl terminal group, to a polymer having polyanhydride terminal group represented by:

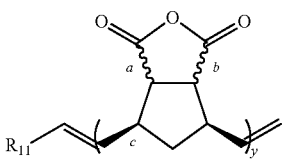

wherein y is an integer between 1 and 20 inclusive, a and b are C—C bonds in cis-configuration with respect to each other and in either cis- or trans-configuration with respect to bond c; and (b) reacting the polymer obtained in (a) with a polyamine represented by

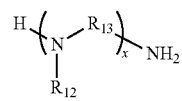

wherein $R_{12}$ is hydrogen or a $C_1$-$C_4$ branched or straight chained alkyl optionally substituted with one or more amine groups, $R_{13}$ is a $C_1$-$C_4$ branched or straight chained alkylene group, and x is an integer between 1 and 10, and further wherein the —$N(R_{12})$—$R_{13}$— unit is optionally interrupted in one or more places by a nitrogen-containing heterocyclic cycloalkyl group, and wherein when the x-th —$N(R_{12})$—$R_{13}$— unit along with the terminal nitrogen atom forms a heterocyclic cycloalkyl group, the terminal —$NH_2$ is replaced by a —NH— group for valency.

According to a further aspect of the disclosed subject matter, a compound prepared by the above method is provided.

According to yet another aspect of the disclosed subject matter, a method for reducing fouling in a hydrocarbon refining process is provided. The method includes providing a crude hydrocarbon for a refining process; and adding an additive to the crude hydrocarbon, the additive being represented by:

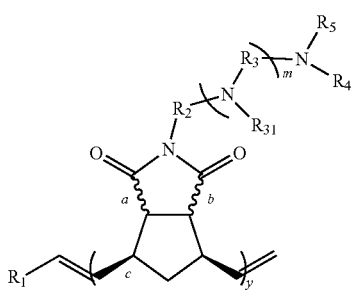

wherein $R_1$ is a branched or straight-chained $C_{10}$-$C_{800}$ alkyl or alkenyl group;

y is an integer between 1 to 20 inclusive;

m is an integer between 0 and 10 inclusive;

a and b are C—C bonds in cis-configuration with respect to each other and in either cis- or trans-configuration with respect to bond c;

$R_2$ and $R_3$ are each independently a $C_1$-$C_4$ branched or straight chained alkylene group;

$R_{31}$ is hydrogen or —$R_8$-$R_9$, wherein either (a) $R_8$ is $C_1$-$C_4$ branched or straight chained alkylene group, and $R_9$ is

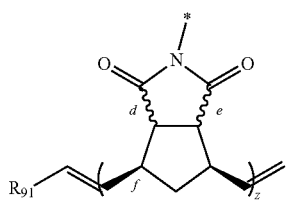

wherein $R_{91}$ is a branched or straight-chained $C_{10}$-$C_{800}$ alkyl or alkenyl group, the asterisk (*) indicates a connecting point with $R_8$, d and e are C—C bonds in cis-configuration with respect to each other and in either cis- or trans-configuration with respect to bond f, and z is an integer between 1 to 20 inclusive; or (b) $R_8$ and $R_9$ together are a $C_1$-$C_4$ branched or straight chained alkyl group optionally substituted with one or more amine groups; and wherein the —N($R_{31}$)—$R_3$— repeat unit is optionally interrupted in one or more places by a nitrogen-containing heterocyclic cycloalkyl group; and wherein $R_4$ and $R_5$ are each independently selected from (a) hydrogen, (b) —$R_6$-$R_7$, wherein $R_6$ is $C_1$-$C_4$ branched or straight chained alkylene group, and $R_7$ is

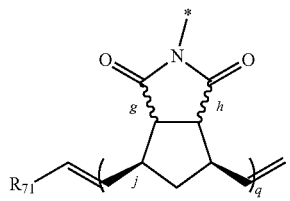

wherein $R_{71}$ is a branched or straight-chained $C_{10}$-$C_{800}$ alkyl or alkenyl group, the asterisk (*) indicates a connecting point with $R_6$, g and h are C—C bonds in cis-configuration with respect to each other and in either cis- or trans-configuration with respect to bond j, and q is an integer between 1 to 20 inclusive; or (c) a bond connected to $R_{31}$ in the m-th —N($R_{31}$)—$R_3$— repeat unit.

In addition, the disclosed subject matter provides the additives as described in the above methods, antifouling compositions comprising such additives, and systems for refining hydrocarbons containing such additives and compositions.

BRIEF DESCRIPTION OF THE DRAWINGS

The disclosed subject matter will now be described in conjunction with the accompanying drawings in which.

DETAILED DESCRIPTION

Definitions

Figure 1:
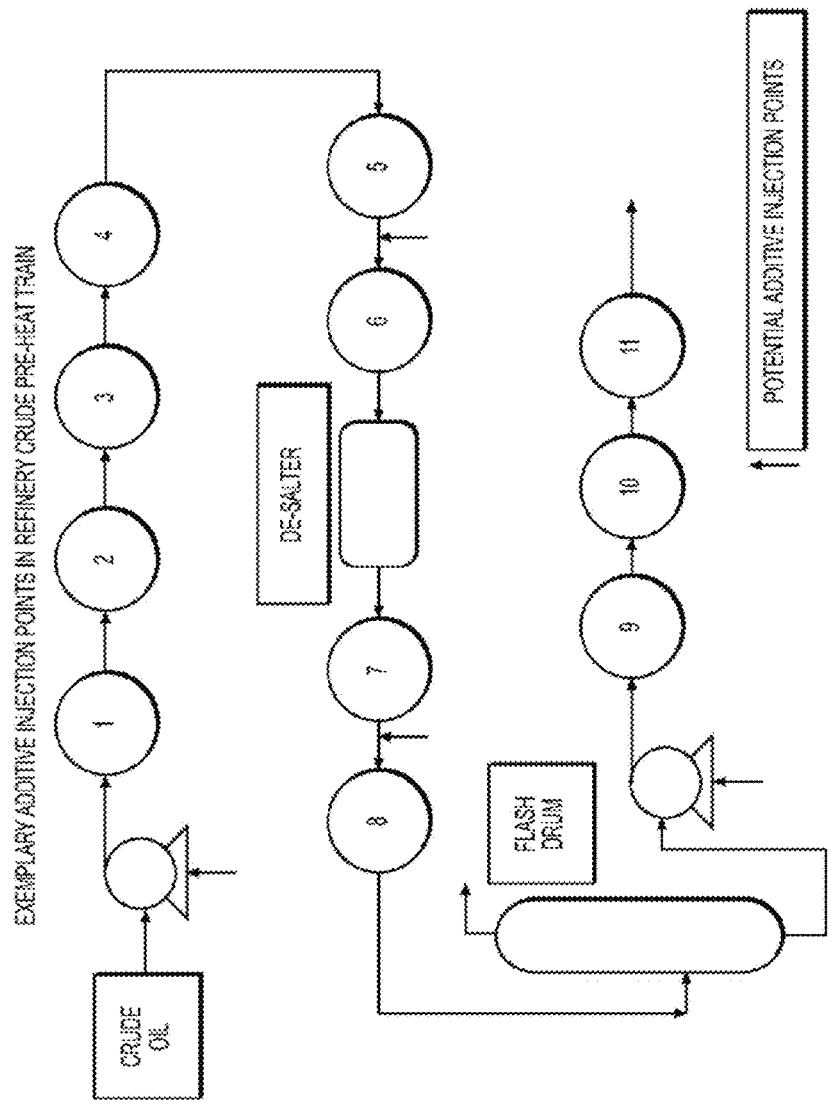
FIG. 1 is a representation of an oil refinery crude pre-heat train, annotated to show non-limiting injection points for the additives of the disclosed subject matter.

The following definitions are provided for purpose of illustration and not limitation.

As used herein, the term "fouling" generally refers to the accumulation of unwanted materials on the surfaces of processing equipment or the like, particularly processing equipment in a hydrocarbon refining process.

As used herein, the term "particulate-induced fouling" generally refers to fouling caused primarily by the presence of variable amounts of organic or inorganic particulates. Organic particulates (such as precipitated asphaltenes and coke particles) include, but are not limited to, insoluble matter precipitated out of solution upon changes in process conditions (e.g., temperature, pressure, or concentration changes) or a change in the composition of the feed stream (e.g., changes due to the occurrence of a chemical reaction). Inorganic particulates include, but are not limited to, silica, iron oxide, iron sulfide, alkaline earth metal oxide, sodium chloride, calcium chloride and other inorganic salts. One major source of these particulates results from incomplete solids removal during desalting and/or other particulate removing processes. Solids promote the fouling of crude oils and blends due to physical effects by modifying the surface area of heat transfer equipment, allowing for longer holdup times at wall temperatures and causing coke formation from asphaltenes and/or crude oil(s).

As used herein, the term "alkyl" refers to a monovalent hydrocarbon group containing no double or triple bonds and arranged in a branched or straight chain.

As used herein, the term "alkylene" refers to a divalent hydrocarbon group containing no double or triple bonds and arranged in a branched or straight chain.

As used herein, the term "alkenyl" refers to a monovalent hydrocarbon group containing one or more double bonds and arranged in a branched or straight chain.

As used herein, a "hydrocarbyl" group refers to any univalent radical that is derived from a hydrocarbon, including univalent alkyl, aryl and cycloalkyl groups.

As used herein, the term "crude hydrocarbon refinery component" generally refers to an apparatus or instrumentality of a process to refine crude hydrocarbons, such as an oil refinery process, which is, or can be, susceptible to fouling. Crude hydrocarbon refinery components include, but are not limited to, heat transfer components such as a heat exchanger, a furnace, a crude preheater, a coker preheater, or any other heaters, a FCC slurry bottom, a debutanizer exchanger/tower, other feed/effluent exchangers and furnace air preheaters in refinery facilities, flare compressor components in refinery facilities and steam cracker/reformer tubes in petrochemical facilities. Crude hydrocarbon refinery components can also include other instrumentalities in which heat transfer can take place, such as a fractionation or distillation column, a scrubber, a reactor, a liquid-jacketed tank, a pipestill, a coker and a visbreaker. It is understood that "crude hydrocarbon refinery components," as used herein, encompasses tubes, piping, baffles and other process transport mechanisms that are internal to, at least partially constitute, and/or are in direct fluid communication with, any one of the above-mentioned crude hydrocarbon refinery components.

As used herein, a reduction (or "reducing") particulate-induced fouling is generally achieved when the ability of particulates to adhere to heated equipment surfaces is reduced, thereby mitigating their impact on the promotion of the fouling of crude oil(s), blends, and other refinery process streams.

As used herein, reference to a group being a particular polymer (e.g., polypropylene or poly(ethylene-co-propylene) encompasses polymers that contain primarily the respective monomer along with negligible amounts of other substitutions and/or interruptions along polymer chain. In other words, reference to a group being a polypropylene group does not require that the group consist of 100% propylene monomers without any linking groups, substitutions, impurities or other substituents (e.g., alkylene or alkenylene substituents). Such impurities or other substituents can be present in relatively minor amounts so long as they do not affect the industrial performance of the additive, as compared to the same additive containing the respective polymer substituent with 100% purity.

For the purposes of the present application, when a polymer is referred to as comprising an olefin, the olefin present in the polymer is the polymerized form of the olefin.

As used herein, a copolymer is a polymer comprising at least two different monomer units (such as propylene and ethylene). A homo-polymer is a polymer comprising units of the same monomer (such as propylene). A propylene polymer is a polymer having at least 50 mole % of propylene.

The term "vinyl termination", also referred to as "allyl chain end(s)" or "vinyl content" is defined to be a polymer having at least one terminus represented by:

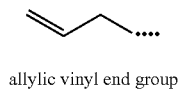

allylic vinyl end group where the "••••" represents the polymer chain.

In a preferred embodiment the allyl chain end is represented by:

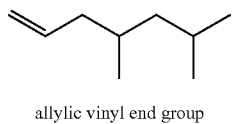

allylic vinyl end group

The amount of allyl chain ends (also called % vinyl termination) is determined using $^1$H NMR at 120° C. using deuterated tetrachloroethane as the solvent on a 500 MHz machine and in selected cases confirmed by $^{13}$C NMR. Resconi has reported proton and carbon assignments (neat perdeuterated tetrachloroethane used for proton spectra while a 50:50 mixture of normal and perdeuterated tetrachloroethane was used for carbon spectra; all spectra were recorded at 100° C. on a Bruker AM 300 spectrometer operating at 300 MHz for proton and 75.43 MHz for carbon) for vinyl terminated propylene polymers in J American Chemical Soc 114 1992, 1025-1032, hereby incorporated by reference in its entirety, that are useful herein.

"Isobutyl chain end" is defined to be a polymer having at least one terminus represented by the formula:

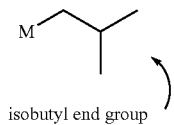

isobutyl end group where M represents the polymer chain. In an example embodiment, the isobutyl chain end is represented by one of the following formulae:

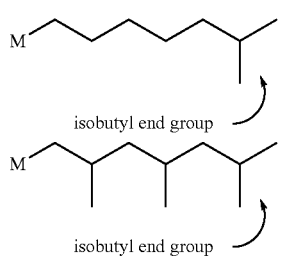

isobutyl end group

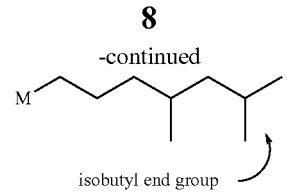

isobutyl end group

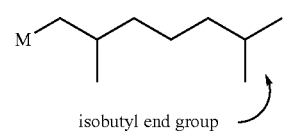

isobutyl end group where M represents the polymer chain.

The "isobutyl chain end to allylic vinyl group ratio" is defined to be the ratio of the percentage of isobutyl chain ends to the percentage of allylic vinyl groups.

As used herein, the term "polymer" refers to a chain of monomers having a Mn of 100 g/mol and above.

Reference will now be made to various aspects of the disclosed subject matter in view of the definitions above.

In one aspect, the additives of the disclosed subject matter can interact with the materials in crude oils in a refinery or the like that are prone to cause fouling, e.g., particulate impurities/contaminants and asphaltenes. The interaction can be physical or chemical such as absorption, association, or chemical bonding. The fouling materials can be rendered more soluble in the crude oils as a result of interaction with the antifouling additives, therefore the fouling on the exchanger metal surfaces can be reduced or eliminated.

In accordance with one aspect of the disclosed subject matter, a compound (additive) is provided, represented by

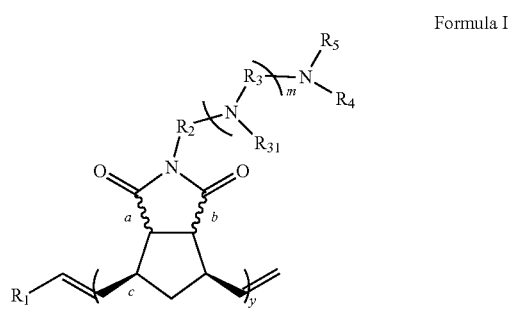

Formula I wherein $R_1$ is a branched or straight-chained $C_{10}$-$C_{800}$ alkyl or alkenyl group;

y is an integer between 1 to 20 inclusive;

m is an integer between 0 and 10 inclusive;

a and b are C—C bonds in cis-configuration with respect to each other and in either cis- or trans-configuration with respect to bond c;

$R_2$ and $R_3$ are each independently a $C_1$-$C_4$ branched or straight chained alkylene group;

$R_{31}$ is hydrogen or —$R_8$-$R_9$, wherein either (a) $R_8$ is $C_1$-$C_4$ branched or straight chained alkylene group, and $R_9$ is

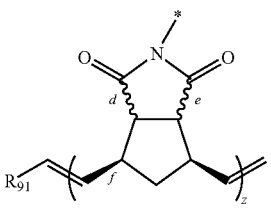

wherein $R_{91}$ is a branched or straight-chained $C_{10}$-$C_{800}$ alkyl or alkenyl group, the asterisk (*) indicates a connecting point with $R_8$, d and e are C—C bonds in cis-configuration with respect to each other and in either cis- or trans-configuration with respect to bond f, and z is an integer between 1 to 20 inclusive; or (b) $R_8$ and $R_9$ together are a $C_1$-$C_4$ branched or straight chained alkyl group optionally substituted with one or more amine groups; and wherein the —N($R_{31}$)—$R_3$— repeat unit is optionally interrupted in one or more places by a nitrogen-containing heterocyclic cycloalkyl group; and wherein $R_4$ and $R_5$ are each independently selected from (a) hydrogen, (b) —$R_6$-$R_7$, wherein $R_6$ is $C_1$-$C_4$ branched or straight chained alkylene group, and $R_7$ is

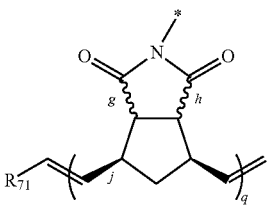

wherein $R_{71}$ is a branched or straight-chained $C_{10}$-$C_{800}$ alkyl or alkenyl group, the asterisk (*) indicates a connecting point with $R_6$, g and h are C—C bonds in cis-configuration with respect to each other and in either cis- or trans-configuration with respect to bond j, and q is an integer between 1 to 20 inclusive; or (c) a bond connected to $R_{31}$ in the m-th —N($R_{31}$)—$R_3$— repeat unit. In certain embodiments of the compound, y can be an integer between 1 and 10 inclusive, or between 1 and 5 inclusive.

In certain embodiments, at least one of $R_1$, $R_{71}$, and $R_{91}$ of the compound of Formula I shown above comprises polypropylene (PP), which can be atactic polypropylene or isotactic polypropylene. The polypropylene can be amorphous, and can include isotactic or syndiotactic crystallizable units. In some embodiments, the polypropylene includes meso diads constituting from about 30% to about 99.5% of the total diads of the polypropylene. In alternative embodiments, at least one of $R_1$, $R_{71}$, and $R_{91}$ of the compound of Formula I comprises polyethylene (PE).

In a further embodiment, at least one of $R_1$, $R_{71}$, and $R_{91}$, of the additive of Formula I comprises poly(ethylene-co-propylene) (EP). The mole percentage of the ethylene units and propylene units in the poly(ethylene-co-propylene) can vary. For example, in some embodiments, the poly(ethylene-co-propylene) can contain about 1 to about 90 mole % of ethylene units and about 99 to about 10 mole % propylene units. In other embodiments, the poly(ethylene-co-propylene) can contain about 10 to about 90 mole % of ethylene units and about 90 to about 10 mole % propylene units. In certain embodiments, the poly(ethylene-co-propylene) contains about 20 to about 50 mole % of ethylene units.

In some embodiments of the above method, at least one of $R_1$, $R_{71}$, and $R_{91}$ of the additive of Formula I has a number-averaged molecular weight of from about 300 to about 30,000 g/mol (assuming one olefin unsaturation per chain, as measured by $^1$H-NMR). Alternatively, at least one of $R_1$, $R_{71}$, and $R_{91}$ of the additive of Formula I has a number-averaged molecular weight of from about 500 to 5,000 g/mol. In one embodiment, the PP or EP included in the $R_1$, $R_{71}$, and $R_{91}$ of the additive Formula I, individually, has a molecular weight (Mn) from about 300 to about 30,000 g/mol, or from about 500 to about 5000 g/mol. In one embodiment, the PP or EP groups have a molecular weight, individually, ranging from about 500 to about 2500 g/mol, or a molecular of from about 500 to about 650 g/mol, or a molecular weight of from about 800 to about 1000 g/mol, or a molecular weight of from about 2000 to about 2500 g/mol.

In other embodiments of the compound, at least one of $R_1$, $R_{71}$, and $R_{91}$ comprises poly(higher alpha-olefin) or poly(propylene-co-higher alpha-olefin), the higher alpha-olefin including two or more carbon atoms on each side chain. For example, suitable higher alpha-olefins can include, but are not limited to, 1-butene, 1-pentene, 1-hexene, 1-heptene, 1-octene, 1-nonene, 1-decene, 1-undecene, 1-dodecene, 1-tridecene, 1-tetradecene, 1-hexadecene, 1-octadecene and the like.

In certain embodiments of the above compound, the nitrogen content in the compound of Formula I is about 1 wt % to about 10 wt % based on the total weight of the compound.

In certain embodiments, $R_3$ is —$CH_2$—$CH_2$—, and $R_{31}$ is hydrogen. In these embodiments, the —N($R_{31}$)—$R_3$— repeat unit can be interrupted in one or more places by a 1,4-diethylenediamine.

In accordance with another aspect of the subject matter disclosed herein, a method is provided for preparing a compound (or additive), such as the compound described above. The method includes:

(a) converting a polymer base unit $R_{11}$, which is a branched or straight-chained $C_{10}$-$C_{800}$ alkyl or alkenyl group having a vinyl terminal group, to a polymer having polyanhydride terminal group represented by:

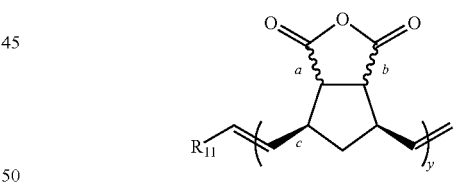

wherein y is an integer between 1 and 20 inclusive, a and b are C—C bonds in cis-configuration with respect to each other and in either cis- or trans-configuration with respect to bond c; and (b) reacting the polymer obtained in (a) with a polyamine represented by

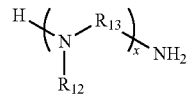

wherein $R_{12}$ is hydrogen or a $C_1$-$C_4$ branched or straight chained alkyl optionally substituted with one or more amine groups, $R_{13}$ is a $C_1$-$C_4$ branched or straight chained alkylene group, and x is an integer between 1 and 10, and further wherein the —N($R_{12}$)—$R_{13}$— unit is optionally interrupted in one or more places by a nitrogen-containing heterocyclic cycloalkyl group, and wherein when the x-th —N($R_{12}$)—$R_{13}$— unit along with the terminal nitrogen atom forms a heterocyclic cycloalkyl group, the terminal —$NH_2$ is replaced by a —NH— group for valency.

In certain embodiments of the compound, y can be an integer between 1 and 10 inclusive, or between 1 and 5 inclusive.

In certain embodiments of the above method, the polymer base unit $R_{11}$ has a number-averaged molecular weight of 300 to 30,000 g/mol (assuming one olefin unsaturation per chain, as measured by $^1$H NMR), and alternatively, about 500 to 5,000 g/mol.

In some embodiments of the above method, the polymer base unit $R_{11}$ comprises polypropylene. The polypropylene can be either atactic polypropylene or isotactic polypropylene. The polypropylene can be amorphous, and can include isotactic or syndiotactic crystallizable units. In some embodiments, the polypropylene includes meso diads constituting from about 30% to about 99.5% of the total diads of the polypropylene. The polymer base unit $R_{11}$ can also comprise polyethylene.

In alternative embodiments, the polymer base unit $R_{11}$ comprises poly(ethylene-co-propylene). The poly(ethylene-co-propylene) can contain from about 1 or 10 mole % to about 90 or 99 mole % of ethylene units and from about 99 or 90 mole % to about 10 or 1 mole % propylene units. In one embodiment, the poly(ethylene-co-propylene) polymer contains from about 2 or 20 mole % to about 50 mole % ethylene units.

In one embodiment, the PP or EP included in the $R_{11}$ of the additive Formula I, individually, have a number-averaged molecular weight ($M_n$) from about 300 to about 30,000 g/mol, or from about 500 to about 5000 g/mol (assuming one olefin unsaturation per chain, as measured by $^1$H NMR). In one embodiment, the PP or EP groups have a molecular weight, individually, ranging from about 500 to about 2500 g/mol, or a molecular of from about 500 to about 650 g/mol, or a molecular weight of from about 800 to about 1000 g/mol, or a molecular weight of from about 2000 to about 2500 g/mol.

In embodiments where the polymer base unit $R_{11}$ include polypropylene or poly(ethylene-co-propylene), such groups can be prepared, for example, by metallocene-catalyzed polymerization of propylene or a mixture of ethylene and propylene, which are then terminated with a high vinyl group content in the chain end. The number-averaged molecular weight ($M_n$) of the PP or EP can be from about 300 to about 30,000 g/mol, as determined by $^1$H NMR spectroscopy. The vinyl-terminated atactic or isotactic polypropylenes (v-PP) or vinyl-terminated poly(ethylene-co-propylene) (v-EP) suitable for further chemical functionalization can have a molecular weight ($M_n$) approximately from about 300 to about 30,000 g/mol, and preferably about 500 to 5,000 g/mol. The terminal olefin group can be a vinylidene group or an allylic vinyl group (both covered in Formula I). In certain embodiments, the terminal olefin group is an allylic vinyl group. In this regard, the terminal allylic vinyl group rich PP or EP as disclosed in U.S. Pat. No. 8,372,930 and co-pending application, U.S. Patent Application Publication No. 20090318646, can be used, each of which is hereby incorporated by reference in its entirety. Some of the vinyl terminated EP or PP according to these co-pending applications contains more than 90% of allylic terminal vinyl group.

In some embodiments of the above method, $R_{11}$ can comprise propylene and less than 0.5 wt % comonomer, preferably 0 wt % comonomer, wherein the $R_{11}$ has:
i) at least 93% allyl chain ends (preferably at least 95%, preferably at least 97%, preferably at least 98%);
ii) a number average molecular weight (Mn) of about 500 to about 20,000 g/mol, as measured by $^1$H NMR, assuming one olefin unsaturation per chain (preferably 500 to 15,000, preferably 700 to 10,000, preferably 800 to 8,000 g/mol, preferably 900 to 7,000, preferably 1000 to 6,000, preferably 1000 to 5,000);
iii) an isobutyl chain end to allylic vinyl group ratio of 0.8:1 to 1.3:1.0;
iv) less than 1400 ppm aluminum, (preferably less than 1200 ppm, preferably less than 1000 ppm, preferably less than 500 ppm, preferably less than 100 Ppm).

In some embodiments of the above method, $R_{11}$ can comprise a propylene copolymer having an Mn of 300 to 30,000 g/mol as measured by 1H NMR and assuming one olefin unsaturation per chain (preferably 400 to 20,000, preferably 500 to 15,000, preferably 600 to 12,000, preferably 800 to 10,000, preferably 900 to 8,000, preferably 900 to 7,000 g/mol), comprising 10 to 90 mol % propylene (preferably 15 to 85 mol %, preferably 20 to 80 mol %, preferably 30 to 75 mol %, preferably 50 to 90 mol %) and 10 to 90 mol % (preferably 85 to 15 mol %, preferably 20 to 80 mol %, preferably 25 to 70 mol %, preferably 10 to 50 mol %) of one or more alpha-olefin comonomers (preferably ethylene, butene, hexene, or octene, or decene, preferably ethylene), wherein the polymer has at least X % allyl chain ends (relative to total unsaturations), where X is 80% or more, preferably 85% or more, preferably 90% or more, preferably 95% or more. Alternatively, $R_{11}$ can have at least 80% isobutyl chain ends (based upon the sum of isobutyl and n-propyl saturated chain ends), preferably at least 85% isobutyl chain ends, preferably at least 90% isobutyl chain ends. Alternately, $R_{11}$ can have an isobutyl chain end to allylic vinyl group ratio of 0.8:1 to 1.35:1.0, preferably 0.9:1 to 1.20:1.0, preferably 0.9:1.0 to 1.1:1.0.

In other embodiments, $R_{11}$ can comprise a polypropylene copolymer having more than 90 mol % propylene (preferably 95 to 99 mol %, preferably 98 to 9 mol %) and less than 10 mol % ethylene (preferably 1 to 4 mol %, preferably 1 to 2 mol %), wherein the copolymer has:
at least 93% allyl chain ends (preferably at least 95%, preferably at least 97%, preferably at least 98%);
a number average molecular weight (Mn) of about 400 to about 30,000 g/mol, as measured by $^1$H NMR and assuming one olefin unsaturation per chain (preferably 500 to 20,000, preferably 600 to 15,000, preferably 700 to 10,000 g/mol, preferably 800 to 9,000, preferably 900 to 8,000, preferably 1000 to 6,000);
an isobutyl chain end to allylic vinyl group ratio of 0.8:1 to 1.35:1.0, and
less than 1400 ppm aluminum, (preferably less than 1200 ppm, preferably less than 1000 ppm, preferably less than 500 ppm, preferably less than 100 ppm).

In alternative embodiments, $R_{11}$ can comprise a polypropylene copolymer comprising:
at least 50 (preferably 60 to 90, preferably 70 to 90) mol % propylene and from 10 to 50 (preferably 10 to 40, preferably 10 to 30) mol % ethylene, wherein the polymer has:
at least 90% allyl chain ends (preferably at least 91%, preferably at least 93%, preferably at least 95%, preferably at least 98%);

a Mn of about 150 to about 20,000 g/mol, as measured by $^1$H-NMR and assuming one olefin unsaturation per chain (preferably 200 to 15,000, preferably 250 to 15,000, preferably 300 to 10,000, preferably 400 to 9,500, preferably 500 to 9,000, preferably 750 to 9,000); and an isobutyl chain end to allylic vinyl group ratio of 0.8:1 to 1.3:1.0, wherein monomers having four or more carbon atoms are present at from 0 to 3 mol % (preferably at less than 1 mol %, preferably less than 0.5 mol %, preferably at 0 mol %).

In further embodiments, $R_{11}$ can comprise a polypropylene copolymer comprising:

at least 50 (preferably at least 60, preferably 70 to 99.5, preferably 80 to 99, preferably 90 to 98.5) mol % propylene, from 0.1 to 45 (preferably at least 35, preferably 0.5 to 30, preferably 1 to 20, preferably 1.5 to 10) mol % ethylene, and from 0.1 to 5 (preferably 0.5 to 3, preferably 0.5 to 1) mol % $C_4$ to $C_{12}$ olefin (such as butene, hexene or octene, or decene, preferably butene), wherein the polymer has:

at least 90% allyl chain ends (preferably at least 91%, preferably at least 93%, preferably at least 95%, preferably at least 98%);

a number average molecular weight (Mn) of about 150 to about 15,000 g/mol, as measured by $^1$H NMR and assuming one olefin unsaturation per chain (preferably 200 to 12,000, preferably 250 to 10,000, preferably 300 to 10,000, preferably 400 to 9500, preferably 500 to 9,000, preferably 750 to 9,000); and an isobutyl chain end to allylic vinyl group ratio of 0.8:1 to 1.35:1.0.

In certain embodiments, $R_{11}$ can comprise a polypropylene copolymer comprising:

at least 50 (preferably at least 60, preferably 70 to 99.5, preferably 80 to 99, preferably 90 to 98.5) mol % propylene, from 0.1 to 45 (preferably at least 35, preferably 0.5 to 30, preferably 1 to 20, preferably 1.5 to 10) mol % ethylene, and from 0.1 to 5 (preferably 0.5 to 3, preferably 0.5 to 1) mol % diene (such as $C_4$ to $C_{12}$ alpha-omega dienes (such as butadiene, hexadiene, octadiene), norbornene, ethylidene norbornene, vinylnorbornene, norbornadiene, and dicyclopentadiene), wherein the polymer has:

at least 90% allyl chain ends (preferably at least 91%, preferably at least 93%, preferably at least 95%, preferably at least 98%);

a number average molecular weight (Mn) of about 150 to about 20,000 g/mol, as measured by $^1$H NMR and assuming one olefin unsaturation per chain (preferably 200 to 15,000, preferably 250 to 12,000, preferably 300 to 10,000, preferably 400 to 9,500, preferably 500 to 9,000, preferably 750 to 9,000); and an isobutyl chain end to allylic vinyl group ratio of 0.7:1 to 1.35:1.0.

In other embodiments of the method, $R_{11}$ can comprises poly(higher alpha-olefin) or poly(propylene-co-higher alpha-olefin), the higher alpha-olefin including two or more carbon atoms on each side chain. For example, suitable higher alpha-olefins can include, but are not limited to, 1-butene, 1-pentene, 1-hexene, 1-heptene, 1-octene, 1-nonene, 1-decene, 1-undecene, 1-dodecene, 1-tridecene, 1-tetradecene, 1-hexadecene, 1-octadecene and the like.

In certain embodiments, $R_{11}$ includes those vinyl terminated macromonomers disclosed in U.S. Patent Application Publication Nos. 20120245312, 20120245310, 20120245311, 20120245313, and U.S. Provisional Application No. 61/704,604, the disclosure of each of which is incorporated by reference in its entirety herein.

In the above method of preparation, for the reaction of converting a polymer base unit $R_{11}$ having a terminal vinyl functionality, a reaction known as ring opening cross metathesis (ROCM) reaction can be employed. As a general example, the ring opening cross metathesis of a vinyl-terminated polypropylene (PP), ethylene-propylene (EP), or propylene-higher alpha-olefin copolymer with a cyclic olefin, norbornene-exo-2,3-dicarboxylic anhydride, is illustrated in Scheme 1 below.

Scheme 1

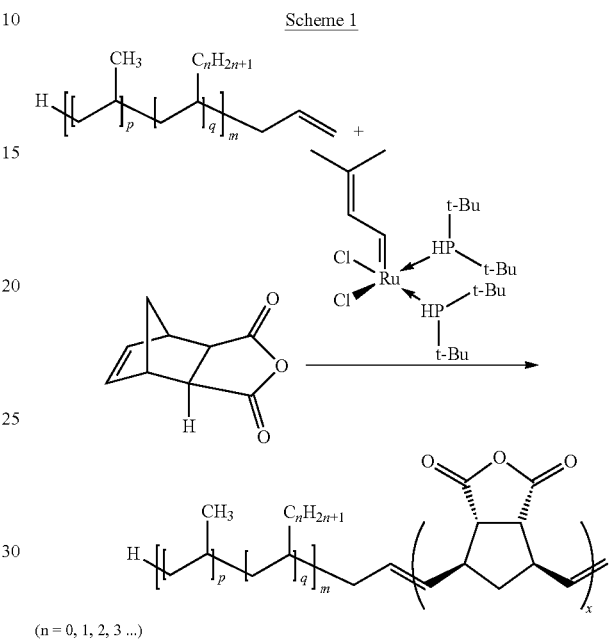

(n = 0, 1, 2, 3 ...)

Other examples of cyclic olefin include norbornene-endo-2,3-dicarboxylic anhydride.

In certain embodiments, the reactants for the ROCM reaction (including the $R_{11}$ and the cyclic olefin) can be combined in a reaction vessel at a temperature of 20° C. to 200° C. (e.g., 50° C. to 160° C., or 60° C. to 140° C.) and a pressure of 0 MPa to 1000 MPa (e.g., 0.5 MPa to 500 MPa, or 1 MPa to 250 MPa) for a residence time of 0.5 seconds to 10 hours (e.g., 1 second to 5 hours, or 1 minute to 1 hour). The molecular weight of the polymer products can be controlled by, inter alia, choice of catalyst, ratio of $R_{11}$ to cyclic olefin, and/or possibly temperature.

As embodied herein, the ROCM reaction is performed in the presence of a metathesis catalyst. Catalysts suitable for the ROCM reaction can include those disclosed in U.S. Pat. Nos. 8,283,419 and 8,063,232; U.S. Patent Application Publication No. 20120309998, the disclosure of each of which is incorporated by reference in its entirety herein. In certain embodiments, the catalyst is a tungsten or ruthenium metal complex-based metathesis catalyst. In certain embodiments, the catalyst is $((t-Bu)_2PH)_2Cl_2Ru=CHCH=C(CH_3)_2$, which can be prepared as described in U.S. Patent Application Publication No. 20120309998.

The quantity of metathesis catalyst employed in the ROCM can be a quantity that provides for an operable metathesis reaction. For example, the ratio of moles of reactants (including cyclic olefins and vinyl terminated macromonomer) to moles of metathesis catalyst can be greater than 10:1, or greater than 100:1, or greater than 1,000:1, or greater than 10,000:1, or greater than 25,000:1, or greater than 50,000:1, or greater than 100,000:1). In some examples, 0.00001 moles to 1.0 moles, or 0.0001 moles to 0.05 moles, or 0.0005 moles to 0.01 moles of catalyst can be charged to the reactor per mole of $R_{11}$ charged.

In some embodiments, the charge ratio of $R_{11}$ to cyclic olefin can be 1:100 to 100:1, or 1:1 to 1:50 depending on the product sought. In some preferred embodiments, the charge ratio of R11 to cyclic olefin is 1:1 to 1:10. In more preferred embodiments, the ratio is 1:5, or more preferably 1:3.

Other conditions and operating parameters of the ROCM reaction include those disclosed in International Application PCT/US2012/059191, the disclosure of which is incorporated by reference in its entirety herein.

As previously noted, the method of preparing the compound can include reacting the polymer obtained above with a polyamine (PAM). The polyamine can include linear, branched or cyclic isomers of an oligomer of ethyleneamine, or mixtures thereof, wherein each two neighboring nitrogens in the oligomer of ethyleneamine are bridged by one or two ethyleneamine groups. For example, the polyamine can be selected from polyethyleneamines with general molecular formula $H_2N(CH_2CH_2NH)_xH$ (where x=1, 2, 3, . . . ) such as ethylenediamine, diethylenetriamine, triethylenetetramine, tetraethylenepentamine, pentaethylenehexamine, hexaethyleneheptamine, and mixtures thereof. In some embodiments, the polyamine can comprise a heavy polyamine, such as polyethyleneamine heavy bottoms available from Dow Chemical as "Heavy Polyamine X" or HPA-X.

For example and as embodied herein, the reaction can include reacting the polymer having polyanhydride terminal group (as illustrated by the product obtained from Scheme 1) with a polyamine to provide the compound as depicted in Scheme 2 below. In certain embodiments, the reaction is conducted at a temperature between ambient temperature and an elevated temperature from 100 to 180 C in an inert solvent for azeotropic removal of water generated by the reaction. Examples of suitable solvents for azeotrope formation with water include benzene, toluene and xylenes. Additional hydrocarbon solvents with a higher boiling point can also be used, preferably with water removal, such as by a vacuum, to drive the reaction to completion. In certain embodiments, the reaction is carried out at ambient pressure. In other embodiments, the reaction is carried out at elevated pressure to increase the rate of reaction, and subsequently under low pressure to facilitate water removal. Reaction times can vary depending on reaction conditions. Generally, no special catalyst is required for the reaction.

Scheme 2

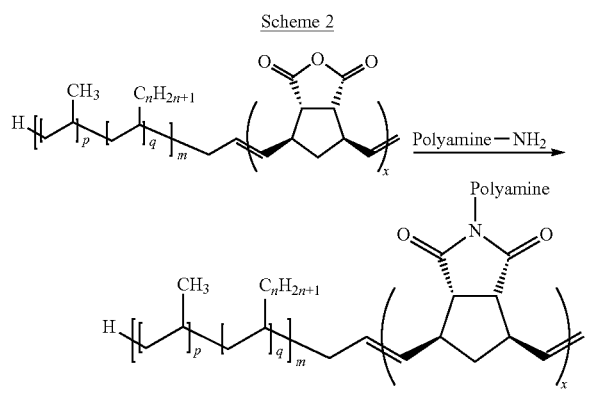

The charge molar ratio of the polymer having the polyanhydride terminal group with the PAM can be from 20:1 to 1:20, and in some embodiments, 5:1 to 1:1, depending on the product sought.

In the above illustrative example, a commercially available heavy polyamine (with about 6.5 nitrogen atoms per molecule on average) from the Dow Chemical Company (Heavy Polyamine X) is used as the polyamine. The number of polymer chain attached to each polyamine molecule can vary from one to two to three or more. In addition, both primary and secondary amino groups on the polyamine can participate in the reaction with the anhydride-functionalized polymer. Other commercially available lower or higher polyamines with linear, branched, cyclic or heterocyclic structures can also be used. It is well-known and understood by those skilled in the art that these polyamines can be mixtures of compounds comprised of molecules with a distribution of chain lengths, different level and type of amine (primary, secondary, and tertiary) functional groups, and varying degree of linear, branched and cyclic structures. For example, possible isomers for tetraethylenepentamine include the following:

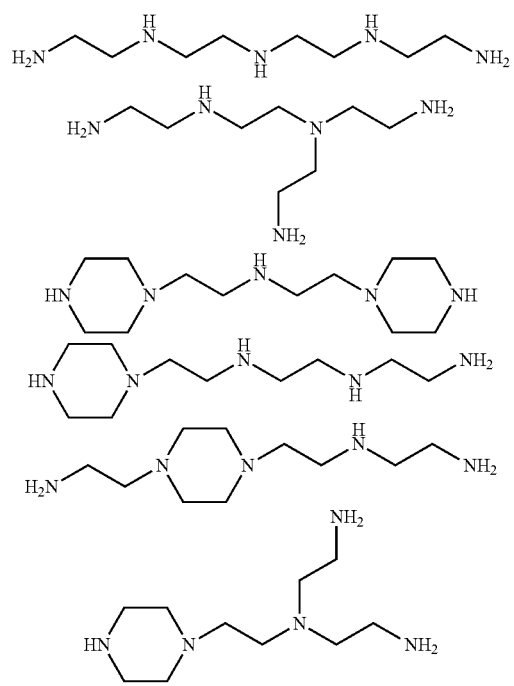

As the molecular weight of polyamines increases, the number of possible isomers increases as well.

In another aspect of the disclosed subject matter, a compound (additive) is prepared by the method discussed above and various embodiments thereof.

In another aspect, and as described further below with regard to an exemplary system, a method for reducing fouling in a hydrocarbon refining process is provided, which comprises providing a crude hydrocarbon for a refining process, and adding to the crude hydrocarbon an additive of Formula I or various embodiments thereof as described above (e.g., at standard operation conditions).

Another aspect of the disclosed subject matter provides a system for refining hydrocarbons that includes at least one crude hydrocarbon refinery component, in which the crude hydrocarbon refinery component includes an additive selected from any one of the additives described herein. The crude hydrocarbon refining component can be selected from a heat exchanger, a furnace, a crude preheater, a coker preheater, a FCC slurry bottom, a debutanizer exchanger, a debutanizer tower, a feed/effluent exchanger, a furnace air preheater, a flare compressor component, a steam cracker, a steam reformer, a distillation column, a fractionation column, a scrubber, a reactor, a liquid-jacketed tank, a pipestill, a coker, and a visbreaker. For example, the crude hydrocarbon refining component can be a heat exchanger (e.g., a crude pre-heat train heat exchanger). Such methods and systems are described in greater details in the following sections and examples.

Another aspect of the disclosed subject matter provides a composition for reducing fouling that includes at least one of any of the above-described additives, and a boronating agent. The boronating agent can be any one or more compounds selected from boric acid, an ortho-borate, or a meta-borate, for example, boric acid, trimethyl metaborate (trimethoxyboroxine), triethyl metaborate, tributyl metaborate, trimethyl borate, triethylborate, triisopropyl borate (triisopropoxyborane), tributyl borate (tributoxyborane) and tri-t-butyl borate. Other boronating agents can be used, such as those disclosed in co-pending applications US20100038290 and US20100170829, each incorporated by reference herein in its entirety.

Further Compositions for Reducing Fouling

The additives of the disclosed subject matter can be used in compositions that prevent fouling, including particulate-induced fouling. In addition to the additives of the disclosed subject matter, the compositions can further contain a hydrophobic oil solubilizer for the additive and/or a dispersant for the additive.

Suitable solubilizers can include, for example, surfactants, carboxylic acid solubilizers, such as the nitrogen-containing phosphorous-free carboxylic solubilizers disclosed in U.S. Pat. No. 4,368,133, hereby incorporated by reference in its entirety.

Also as disclosed in U.S. Pat. No. 4,368,133, hereby incorporated by reference in its entirety, surfactants that can be included in compositions of the disclosed subject matter can include, for example, cationic, anionic, nonionic or amphoteric type of surfactant. See, for example, McCutcheon's "Detergents and Emulsifiers", 1978, North American Edition, published by McCutcheon's Division, MC Publishing Corporation, Glen Rock, N.J., U.S.A., including pages 17-33, which is hereby incorporated by reference in its entirety.

The compositions of the disclosed subject matter can further include, for example, viscosity index improvers, anti-foamants, antiwear agents, demulsifiers, anti-oxidants, and other corrosion inhibitors.

Furthermore, the additives of the disclosed subject matter can be added with other compatible components that address other problems that can present themselves in an oil refining process known to one of ordinary skill in the art.

Uses of the Additives and Compositions in a Refinery Process

The additives of the disclosed subject matter are generally soluble in a typical hydrocarbon refinery stream and can thus be added directly to the process stream, alone or in combination with other additives that either reduce fouling or improve some other process parameter.

The additives can be introduced, for example, upstream from the particular crude hydrocarbon refinery component(s) (e.g., a heat exchanger) in which it is desired to prevent fouling (e.g. particulate-induced fouling). Alternatively, the additive can be added to the crude oil prior to being introduced to the refining process, or at the very beginning of the refining process.

In certain embodiments of the disclosed subject matter, the additive is dissolved in an inert carrier solvent to reduce the material viscosity of the additive. The additive can be dissolved in the carrier solvent by a mechanical blending process. Suitable carrier solvents include but are not limited to naphtha, mineral oil, hydrocarbon fluid and paraffinic oil. For example, the additive is diluted with solvent until the viscosity of the resulting solution is acceptable for pumping and transfer of the additive blend to the crude oil stream at ambient conditions. As embodied herein, the additive is diluted until the resulting solution is acceptable for pumping and transfer of the additive blend to the crude oil stream at ambient conditions in refineries subject to cold climates.

It is noted that water can have a negative impact on boron-containing additives. Accordingly, it is advisable to add boron-containing additives at process locations that have a minimal amount of water.

While not limited thereto, the additives of the disclosed subject matter are particularly suitable in reducing or preventing particulate-induced fouling. Thus one aspect of the disclosed subject matter provides a method of reducing and/or preventing, in particular, particulate-induced fouling that includes adding at least one additive of the disclosed subject matter to a process stream that is known, or believed to contribute to, particulate-induced fouling. To facilitate determination of proper injection points, measurements can be taken to ascertain the particulate level in the process stream. Thus, one embodiment of the disclosed subject matter includes identifying particular areas of a refining process that have relatively high particulate levels, and adding any one of the additives of the disclosed subject matter in close proximity to these areas (e.g., just upstream to the area identified as having high particulate levels).

In some embodiments of the disclosed subject matter, a method to reduce fouling is provided comprising adding any one of the above-mentioned additives or compositions to a crude hydrocarbon refinery component that is in fluid communication with a process stream that contains, at least 50 wppm of particulates, including organic and inorganic particulates. In another embodiment of the disclosed subject matter, a method to reduce fouling is provided comprising adding any one of the above-mentioned antifouling additives or compositions to a crude hydrocarbon refinery component that is in fluid communication with a process stream. In another embodiment of the disclosed subject matter, a method to reduce fouling is provided comprising adding any one of the above-mentioned additives to a crude hydrocarbon refinery component that is in fluid communication with a process stream that contains at least 250 wppm (or 1000 wppm, or 10,000 wppm) of particulates, including organic and inorganic particulates, as defined above.

In some embodiments of the disclosed subject matter, the additives or compositions of the disclosed subject matter are added to selected crude oil process streams known to contain, or possibly contain, problematic amounts of organic or inorganic particulate matter (e.g. 1-10,000 wppm), such as inorganic salts. Accordingly, the additives of the disclosed subject matter can be introduced far upstream, where the stream is relatively unrefined (e.g. the refinery crude pre-heat train). The additives can be also added, for example, after the desalter to counteract the effects of incomplete salt removal or to the bottoms exit stream from the fractionation column to counteract the high temperatures that are conducive to fouling.

FIG. 1 demonstrates possible additive injection points within the refinery crude pre-heat train for the additives of the disclosed subject matter, wherein the numbered circles represent heat exchangers. As shown in FIG. 1, the additives can be introduced in crude storage tanks and at several locations in the preheat train. This includes at the crude charge pump (at the very beginning of the crude pre-heat train), and/or before and after the desalter, and/or to the bottoms stream from a flash drum.

The total amount of additive to be added to the process stream can be determined by a person of ordinary skill in the art. In one embodiment, up to about 1000 wppm of additive is added to the process stream. For example, the additive can be added such that its concentration, upon addition, is about 50 ppm, 250 ppm or 500 ppm. More or less additive can be added depending on, for example, the amount of particulate in the stream, the ΔT associated with the particular process and the degree of fouling reduction desired in view of the cost of the additive.

The additives or compositions of the disclosed subject matter can be added in a solid (e.g. powder or granules) or liquid form directly to the process stream. As mentioned above, the additives or compositions can be added alone, or combined with other components to form a composition for reducing fouling (e.g. particulate-induced fouling). Any suitable technique can be used for adding the additive to the process stream, as known by a person of ordinary skill in the art in view of the process to which it is employed. As a non-limiting example, the additives or compositions can be introduced via injection that allows for sufficient mixing of the additive and the process stream.

EXAMPLES

The disclosed subject matter is further described by means of the examples, presented below. The use of such examples is illustrative only and in no way limits the scope and meaning of the disclosed subject matter or of any exemplified term. Likewise, the disclosed subject matter is not limited to any particular preferred embodiments described herein. Indeed, many modifications and variations of the disclosed embodiments will be apparent to those skilled in the art upon reading this specification.

Example 1—Synthesis of Compounds

A. Ring Opening Cross Metathesis Reaction of Norbornene-Exo-2,3-Dicarboxylic Anhydride with Vinyl Terminated Propylene/1-Butene Copolymer The general scheme of the synthesis is shown in Scheme 3 below.

Scheme 3

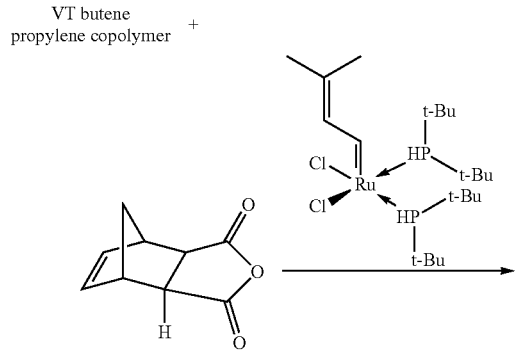

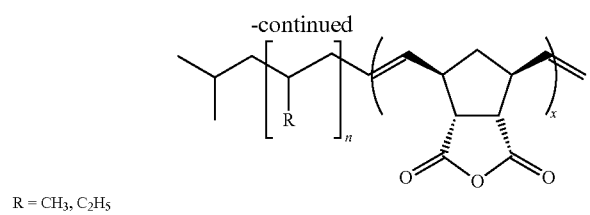

R = CH₃, C₂H₅

An oven dried 250 mL round bottom flask was charged in the drybox with the vinyl terminated propylene/1-butene copolymer (47.0 g, ~27.2 mmol), norbornene-exo-2,3-dicarboxylic anhydride (7.7 g, 46.9 mmol) and CHCl₃ (50 mL). The solution was heated to 50° C. and stirred for two hours to homogenize the poorly soluble anhydride. The solution was analyzed by ¹H-NMR showing a molar ratio of approximately 2 norbornene anhydride to one vinyl terminated butene-propylene copolymer vinyl group. The catalyst, ((t-Bu)₂PH)₂Cl₂Ru=CHCH=C(CH₃)₂, was added in one portion and stirred at 50° C. for 2 hours. The reaction was quenched using 1 g of silica, and the CHCl₃ was removed under vacuum at 45° C. overnight. The translucent brown polymer was treated with approximately 150 mL of pentane. The mixture was heated to 40° C. and stirred for several hours to homogenize the mixture. The mixture was then cooled for 2 hours to −25° C. This mixture was then filtered using a plug of silica, followed by further filtration through 1 micron syringe filters. The solvent was removed under a stream of nitrogen gas. The polymer product was dried by sparging nitrogen gas directly into the polymer while heating it to 80° C. The dried polymer product was obtained as a colorless viscous product (37.9 g) and analyzed by ¹H-NMR: 400 MHz (C₂D₂Cl₄): δ 5.9 (m, 0.32H), 5.3-5.7 (m, 1.35H), 5.1-5.3 (m, 0.57H), 2.75-3.5 (m, 2.51H), 0.5-2.5 (m, 93.9H). ¹H-NMR showed 100% conversion of the vinyl terminated propylene/1-butene copolymer starting material. The degree of ROCM, or number of norbornene anhydride units on the end of the functionalized polymer, was determined to be 2.4 by Method A and was calculated to be 2.2 by Method B below.

Method A

The degree of ROCM was calculated by the ratio of the ¹H-NMR integration of total internal olefin (5.3 ppm-5.7 ppm) to the CH₂ olefin in the functionalized polymer (5.1 ppm-5.3 ppm):

$$\text{Degree of } ROCM \text{ (method A)} = \frac{\int int \text{ olefin}}{\int = CH_2(\text{product})}.$$

Method B

Alternatively, the degree of ROCM can be calculated by the ratio of the ¹H-NMR integration of product ring methine protons (2.75 ppm-3.5 ppm) to the CH₂ olefin in the functionalized polymer (5.1 ppm-5.3 ppm).

$$\text{Degree of } ROCM \text{ (method B)} = \frac{\int \text{methine}}{\int = CH_2(\text{product})} * \frac{1}{2}.$$

The above results indicate that little or no dimerization occurred. Catalyst turn over frequency (TON) was calculated to be 1,820. Molecular weight of the anhydride-functionalized polymer product as measured by GPC was 6855 ($M_w$) and 2888 ($M_n$). Elemental analyses for the polymer product found C: 83.16%, H: 13.40%. The oxygen content of the compound is estimated to be about 3.44 wt %. The anhydride content of this material is estimated to be about 0.717 mmol/g.

B. Functionalization of Anhydride-Functionalized Propylene/1-Butene Copolymer with Heavy Polyamine X (HPA-X)

A solution of Heavy Polyamine X (0.985 g, 3.58) in xylenes (10 ml) was added to a solution of anhydride-functionalized propylene/1-butene copolymer (10.00 g, from Example 1A) in xylenes (65 ml) in a two-neck round-bottomed flask over 5 minutes at room temperature. The resulting mixture was heated in an oil bath at 160° C. for 24 hours under a nitrogen atmosphere. During the reaction an azeotropic mixture of xylenes and water was collected in a Dean-Stark trap. The light brown mixture was cooled to room temperature and excess xylenes was removed on a rotary evaporator. The residual product was further purified by heating at 95° C. under high vacuum to afford a light brown viscous product (10.82 g). Elemental analyses for this propylene/1-butene copolymer-polyamine additive found C: 81.34%, H: 13.07%, N: 3.15%.

Example 2—Fouling Reduction Measured in the Alcor HLPS (Hot Liquid Process Simulator)

Figure 2:
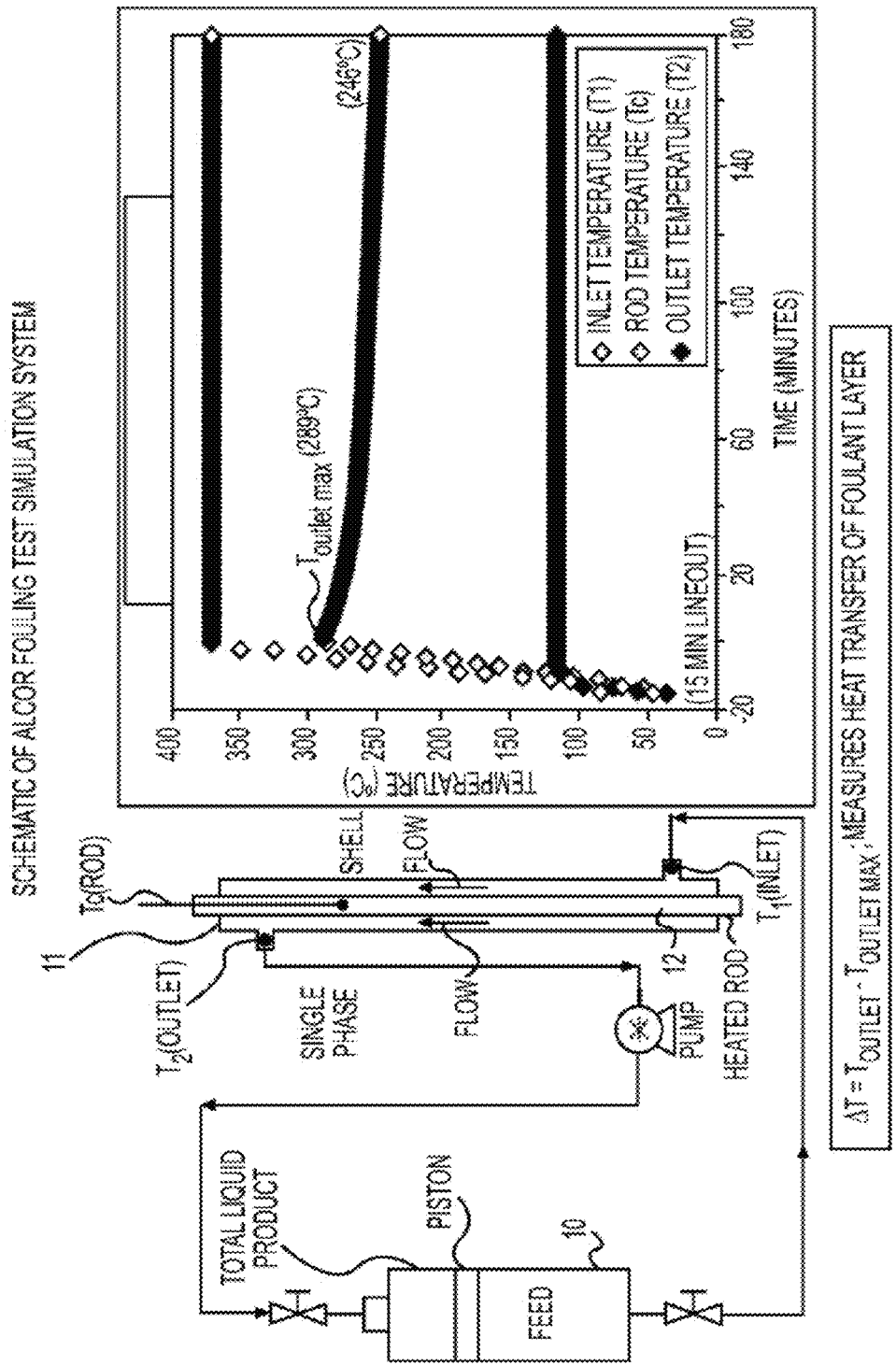
FIG. 2 is a schematic of the Alcor Hot Liquid Process Simulator (HLPS) employed in Example 2 of this application.

FIG. 2 depicts an Alcor HLPS (Hot Liquid Process Simulator) testing apparatus used to measure the impact of addition of particulates to a crude oil on fouling and the impact the addition of an additive of the disclosed subject matter has on the mitigation of fouling. The testing arrangement includes a reservoir 10 containing a feed supply of crude oil. The feed supply of crude oil can contain a base crude oil containing a whole crude or a blended crude containing two or more crude oils. The feed supply is heated to a temperature of approximately 150° C./302° F. and then fed into a shell 11 containing a vertically oriented heated rod 12. The heated rod 12 is formed from carbon-steel (1018). The heated rod 12 simulates a tube in a heat exchanger. The heated rod 12 is electrically heated to a surface temperature of 370° C./698° F. or 400° C./752° F. and maintained at such temperature during the trial. The feed supply is pumped across the heated rod 12 at a flow rate of approximately 3.0 mL/minute. The spent feed supply is collected in the top section of the reservoir 10. The spent feed supply is separated from the untreated feed supply oil by a sealed piston, thereby allowing for once-through operation. The system is pressurized with nitrogen (400-500 psig) to ensure gases remain dissolved in the oil during the test. Thermocouple readings are recorded for the bulk fluid inlet and outlet temperatures and for surface of the rod 12.

During the constant surface temperature testing, foulant deposits and builds up on the heated surface. The foulant deposits are thermally degraded to coke. The coke deposits cause an insulating effect that reduces the efficiency and/or ability of the surface to heat the oil passing over it. The resulting reduction in outlet bulk fluid temperature continues over time as fouling continues. This reduction in temperature is referred to as the outlet liquid ΔT or ΔT and can be dependent on the type of crude oil/blend, testing conditions and/or other effects, such as the presence of salts, sediment or other fouling promoting materials. A standard Alcor fouling test is carried out for 180 minutes. The total fouling, as measured by the total reduction in outlet liquid temperature over time, is plotted on the y-axis of FIG. 3 and is the observed outlet temperature ($T_{outlet}$) minus the maximum observed outlet $T_{outlet\ max}$ (presumably achieved in the absence of any fouling).

Figure 3:
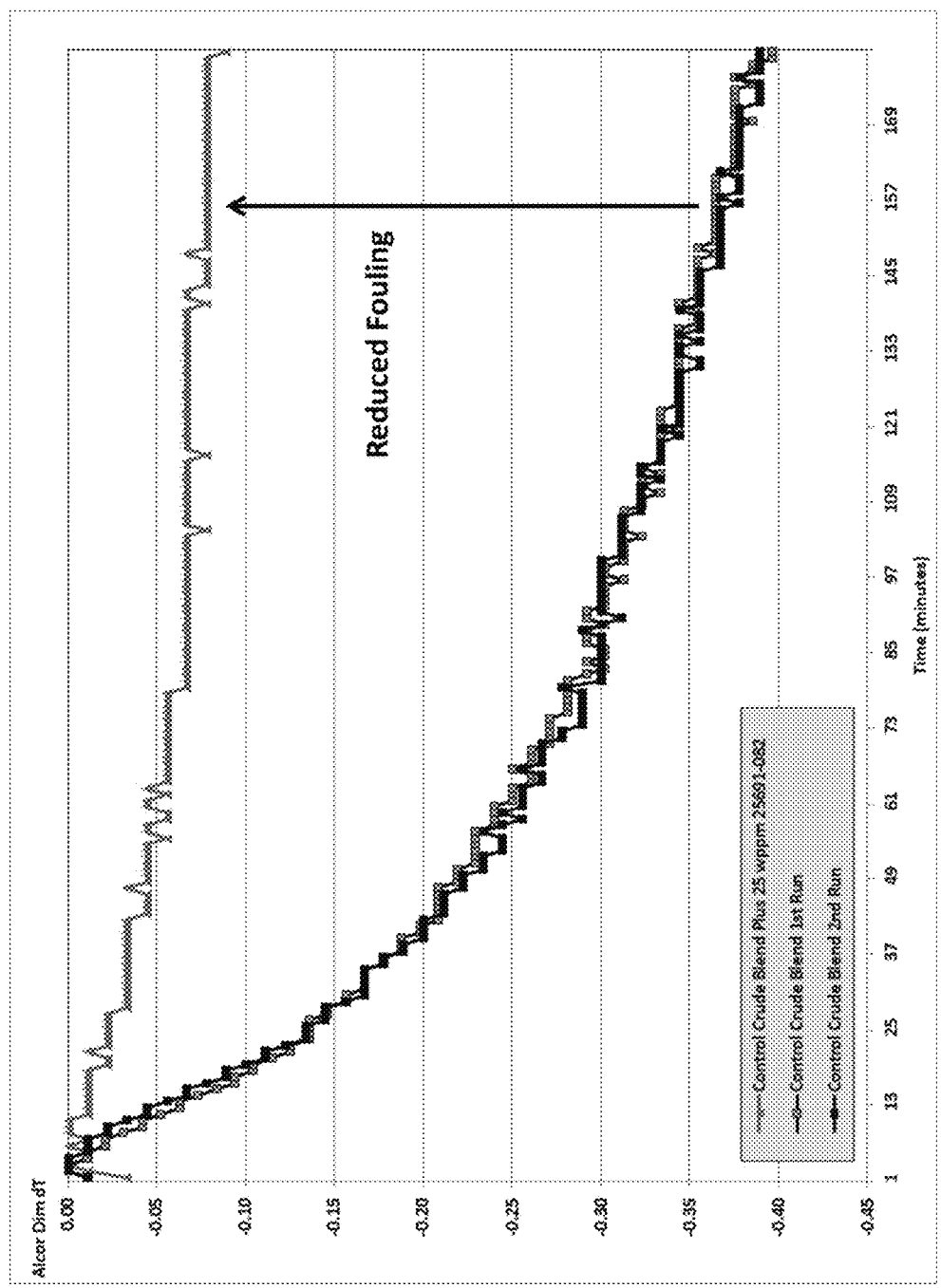
FIG. 3 is a graph demonstrating the effects of fouling of a control crude oil blend sample and a crude oil blend sample treated with 25 wppm of an additive according to the disclosed subject matter, as measured by the Alcor HLPS apparatus depicted in FIG. 2.

FIG. 3 illustrates the impact of fouling of a refinery component over 180 minutes. Two blends were tested in the Alcor unit: a crude oil control containing added rust (iron oxide) particles (200 wppm) without an additive, and the same stream with 25 wppm of the additive prepared according to the method in Example 1.B. above. As FIG. 3 demonstrates, the reduction in the outlet temperature over time (due to fouling) is less for the process blend containing 25 wppm of additive as compared to the crude oil control without the additive. This indicates that the additive is effective at reducing fouling of a heat exchanger.

Additional Embodiments

Additionally or alternatively, the disclosed subject matter can include one or more of the following embodiments.

The Embodiment 1: A compound represented by:

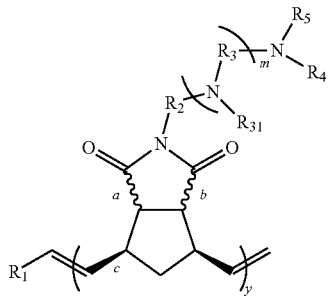

wherein $R_1$ is a branched or straight-chained $C_{10}$-$C_{800}$ alkyl or alkenyl group; y is an integer between 1 to 20 inclusive; m is an integer between 0 and 10 inclusive; a and b are C—C bonds in cis-configuration with respect to each other and in either cis- or trans-configuration with respect to bond c; $R_2$ and $R_3$ are each independently a $C_1$-$C_4$ branched or straight chained alkylene group; $R_{31}$ is hydrogen or —$R_8$-$R_9$, wherein either (a) $R_8$ is $C_1$-$C_4$ branched or straight chained alkylene group, and $R_9$ is

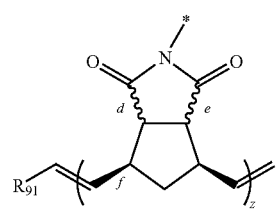

wherein $R_{91}$ is a branched or straight-chained $C_{10}$-$C_{800}$ alkyl or alkenyl group, the asterisk (*) indicates a connecting point with $R_8$, d and e are C—C bonds in cis-configuration with respect to each other and in either cis- or trans-configuration with respect to bond f, and z is an integer between 1 to 20 inclusive; or (b) $R_8$ and $R_9$ together are a $C_1$-$C_4$ branched or straight chained alkyl group optionally substituted with one or more amine groups; and wherein the —N($R_{13}$)—$R_3$— repeat unit is optionally interrupted in one or more places by a nitrogen-containing heterocyclic cycloalkyl group; and wherein $R_4$ and $R_5$ are each independently selected from (a) hydrogen, (b) —$R_6$-$R_7$, wherein $R_6$ is $C_1$-$C_4$ branched or straight chained alkylene group, and $R_7$ is

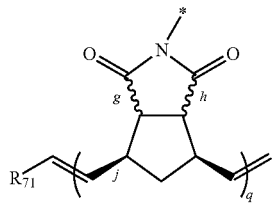

wherein $R_{71}$ is a branched or straight-chained $C_{10}$-$C_{800}$ alkyl or alkenyl group, the asterisk (*) indicates a connecting point with $R_6$, g and h are C—C bonds in cis-configuration with respect to each other and in either cis- or trans-configuration with respect to bond j, and q is an integer between 1 to 20 inclusive; or (c) a bond connected to $R_{31}$ in the m-th —N($R_{13}$)—$R_3$— repeat unit.

Embodiment 2: The compound of Embodiment 1, wherein at least one of $R_1$, $R_{71}$, and $R_{91}$ comprises polypropylene.

Embodiment 3: The compound of Embodiment 2, wherein the polypropylene is atactic polypropylene, isotactic polypropylene, or syndiotactic polypropylene.

Embodiment 4: The compound of Embodiment 2, wherein the polypropylene is amorphous.

Embodiment 5: The compound of Embodiment 2, wherein the polypropylene includes isotactic or syndiotactic crystallizable units.

Embodiment 6: The compound of Embodiment 2, wherein the polypropylene includes meso diads constituting from about 30% to about 99.5% of the total diads of the polypropylene.

Embodiment 7: The compound of Embodiment 2, wherein at least one of $R_1$, $R_{71}$, and $R_{91}$ has a number-averaged molecular weight of from about 300 to about 30000 g/mol.

Embodiment 8: The compound of Embodiment 7, wherein at least one of $R_1$, $R_{71}$, and $R_{91}$ has a number-averaged molecular weight of from about 500 to about 5000 g/mol.

Embodiment 9: The compound of Embodiment 1, wherein at least one of $R_1$, $R_{71}$, and $R_{91}$ comprises polyethylene.

Embodiment 10: The compound of Embodiment 1, wherein at least one of $R_1$, $R_{71}$, and $R_{91}$ comprises poly(ethylene-co-propylene).

Embodiment 11: The compound of Embodiment 10, wherein at least one of $R_1$, $R_{71}$, and $R_{91}$ comprises from about 1 mole % to about 90 mole % of ethylene units and from about 99 mole % to about 10 mole % propylene units.

Embodiment 12: The compound of Embodiment 11, wherein at least one of $R_1$, $R_{71}$, and $R_{91}$ comprises from about 10 mole % to about 50 mole % of ethylene units.

Embodiment 13: The compound of Embodiment 1, wherein at least one of $R_1$, $R_{71}$, and $R_{91}$ comprises poly(higher alpha-olefin), the higher alpha-olefin including two or more carbon atoms on each side chain.

Embodiment 14: The compound of Embodiment 1, wherein at least one of $R_1$, $R_{71}$, and $R_{91}$ comprises poly(propylene-co-higher alpha-olefin), the higher alpha-olefin including two or more carbon atoms on each side chain.

Embodiment 15: The compound according to any one of the previous Embodiments, wherein the nitrogen content in the compound is about 1 wt % to about 10 wt % based on the total weight of the compound.

Embodiment 16: The compound according to any one of the previous Embodiments, wherein $R_3$ is —$CH_2$—$CH_2$—, and $R_{31}$ is hydrogen.

Embodiment 17: The compound of Embodiment 16, wherein the —N($R_{31}$)—$R_3$— repeat unit is interrupted in one or more places by a 1,4-diethylenediamine.

Embodiment 18: A method for preparing a compound, comprising: (a) converting a polymer base unit $R_{11}$, which is a branched or straight-chained $C_{10}$-$C_{800}$ alkyl or alkenyl group having a vinyl terminal group, to a polymer having polyanhydride terminal group represented by:

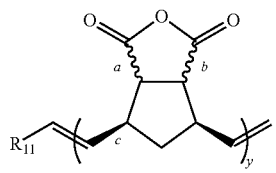

wherein y is an integer between 1 and 20 inclusive, a and b are C—C bonds in cis-configuration with respect to each other and in either cis- or trans-configuration with respect to bond c; and (b) reacting the polymer obtained in (a) with a polyamine represented by

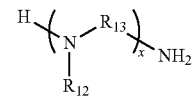

wherein $R_{12}$ is hydrogen or a $C_1$-$C_4$ branched or straight chained alkyl optionally substituted with one or more amine groups, $R_{13}$ is a $C_1$-$C_4$ branched or straight chained alkylene group, and x is an integer between 1 and 10, and further wherein the —N($R_{12}$)—$R_{13}$— unit is optionally interrupted in one or more places by a nitrogen-containing heterocyclic cycloalkyl group, and wherein when the x-th —N($R_{12}$)—$R_{13}$— unit along with the terminal nitrogen atom forms a heterocyclic cycloalkyl group, the terminal —$NH_2$ is replaced by a —NH— group for valency.

Embodiment 19: The method of Embodiment 18, wherein $R_{11}$ comprises polypropylene.

Embodiment 20: The method of Embodiment 19, wherein the polypropylene is atactic polypropylene, isotactic polypropylene, or syndiotactic polypropylene.

Embodiment 21: The method of Embodiment 19, wherein the polypropylene is amorphous.

Embodiment 22: The method of Embodiment 19, wherein the polypropylene includes isotactic or syndiotactic crystallizable units.

Embodiment 23: The method of Embodiment 19, wherein the polypropylene includes meso diads constituting from about 30% to about 99.5% of the total diads of the polypropylene.

Embodiment 24: The method of Embodiment 18, wherein the molar ratio of $R_{11}$:polyamine is between about 5:1 and about 1:5.

Embodiment 25: The method of Embodiment 18, wherein $R_{11}$ has a number-averaged molecular weight of from about 300 to about 30000 g/mol.

Embodiment 26: The method of Embodiment 25, wherein $R_{11}$ has a number-averaged molecular weight of from about 500 to about 5000 g/mol.

Embodiment 27: The method of Embodiment 18, wherein $R_{11}$ comprises polyethylene.

Embodiment 28: The method of Embodiment 18, wherein $R_{11}$ comprises poly(ethylene-co-propylene).

Embodiment 29: The method of Embodiment 18, wherein $R_{11}$ comprises from about 10 mole % to about 90 mole % of ethylene units and from about 90 mole % to about 10 mole % propylene units.

Embodiment 30: The method of Embodiment 29, wherein $R_{11}$ comprises from about 20 mole % to about 50 mole % of ethylene units.

Embodiment 31: The method of Embodiment 18, wherein $R_{11}$ comprises poly(higher alpha-olefin), the higher alpha-olefin including two or more carbon atoms on each side chain.

Embodiment 32: The method of Embodiment 18, wherein $R_{11}$ comprises poly(propylene-co-higher alpha-olefin), the higher alpha-olefin including two or more carbon atoms on each side chain.

Embodiment 33: The method of Embodiment 18, wherein $R_{11}$ comprises poly(ethylene-co-higher alpha-olefin), the higher alpha-olefin including two or more carbon atoms on each side chain.

Embodiment 34: The method of Embodiment 18, wherein at least 50% of the terminal vinyl groups of $R_{11}$ are an allylic vinyl group.

Embodiment 35: The method of Embodiment 18, wherein the polyamine comprises linear, branched or cyclic isomers of an oligomer of ethyleneamine, or mixtures thereof, wherein each two neighboring nitrogens in the oligomer of ethyleneamine are bridged by one or two ethyleneamine groups.

Embodiment 36: The method of Embodiment 35, wherein the polyamine is selected from ethylenediamine, diethylenetriamine, triethylenetetramine, tetraethylenepentamine, pentaethylenehexamine, hexaethyleneheptamine, and mixtures thereof.

Embodiment 37: The method of Embodiment 18, wherein the polyamine comprises a heavy polyamine.

Embodiment 38: The method of Embodiment 18, wherein (a) comprises reacting the polymer having the terminal vinyl group with norbornene-exo-2,3-dicarboxylic anhydride.

Embodiment 39: The method of Embodiment 18, wherein (a) comprises reacting the polymer having the terminal vinyl group with norbornene-endo-2,3-dicarboxylic anhydride.

Embodiment 40: The method of Embodiment 18, wherein the reaction in (a) is a ring opening cross metathesis reaction catalyzed by a tungsten or ruthenium metal complex-based metathesis catalyst.

Embodiment 41: A compound produced by the method of any of Embodiments 18-40.

Embodiment 42: A method for reducing fouling in a hydrocarbon refining process comprising providing a crude hydrocarbon for a refining process; adding an additive to the crude hydrocarbon, the additive being represented by the compound of any of Embodiments 1-17.

Embodiment 43: A method for reducing fouling in a hydrocarbon refining process comprising providing a crude hydrocarbon for a refining process; and adding an additive to the crude hydrocarbon, the additive being prepared by the method of any of Embodiments 18-40.

Embodiment 44: A system for refining hydrocarbons comprising: at least one crude hydrocarbon refinery component; and crude hydrocarbon in fluid communication with the at least one crude hydrocarbon refinery component, the crude hydrocarbon comprising an additive represented by the compound of any of Embodiments 1-17.

Embodiment 45: The system of Embodiment 44, wherein the at least one crude hydrocarbon refinery component is selected from a heat exchanger, a furnace, a crude preheater, a coker preheater, a FCC slurry bottom, a debutanizer exchanger, a debutanizer tower, a feed/effluent exchanger, a furnace air preheater, a flare compressor component, a steam cracker, a steam reformer, a distillation column, a fractionation column, a scrubber, a reactor, a liquid-jacketed tank, a pipestill, a coker, and a visbreaker.

The disclosed subject matter is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

It is further to be understood that all values are approximate, and are provided for description.

Patents, patent applications, publications, product descriptions, and protocols are cited throughout this application, the disclosures of each of which is incorporated herein by reference in its entirety for all purposes.

What is claimed:

1. A compound represented by:

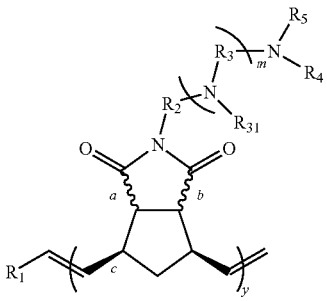

wherein $R_1$ is a branched or straight-chained $C_{10}$-$C_{800}$ alkyl or alkenyl group;

y is an integer between 1 to 20 inclusive;

m is an integer between 0 and 10 inclusive;

a and b are C—C bonds in cis-configuration with respect to each other and in either cis- or trans-configuration with respect to bond c;

$R_2$ and $R_3$ are each independently a $C_1$-$C_4$ branched or straight chained alkylene group;

$R_{31}$ is hydrogen or —$R_8$-$R_9$, wherein either (a) $R_8$ is $C_1$-$C_4$ branched or straight chained alkylene group, and $R_9$ is

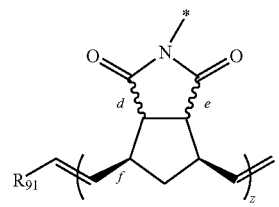

wherein $R_{91}$ is a branched or straight-chained $C_{10}$-$C_{800}$ alkyl or alkenyl group, the asterisk (*) indicates a connecting point with $R_8$, d and e are C—C bonds in cis-configuration with respect to each other and in either cis- or trans-configuration with respect to bond f, and z is an integer between 1 to 20 inclusive; or (b) $R_8$ and $R_9$ together are a $C_1$-$C_4$ branched or straight chained alkyl group optionally substituted with one or more amine groups; and wherein the —N($R_{31}$)—$R_3$— repeat unit is optionally interrupted in one or more places by a nitrogen-containing heterocyclic cycloalkyl group; and wherein $R_4$ and $R_5$ are each independently selected from (a) hydrogen, (b) $R_6$-$R_7$, wherein $R_6$ is $C_1$-$C_4$ branched or straight chained alkylene group, and $R_7$ is

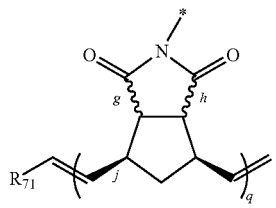

wherein $R_{71}$ is a branched or straight-chained $C_{10}$-$C_{800}$ alkyl or alkenyl group, the asterisk (*) indicates a connecting point with $R_6$, g and h are C—C bonds in cis-configuration with respect to each other and in either cis- or trans-configuration with respect to bond j, and q is an integer between 1 to 20 inclusive; or (c) a bond connected to $R_{31}$ in the m-th —N($R_{31}$)—$R_3$— repeat unit.

2. The compound of claim 1, wherein at least one of $R_1$, $R_{71}$, and $R_{91}$ comprises polypropylene.

3. The compound of claim 2, wherein the polypropylene is atactic polypropylene, isotactic polypropylene, or syndiotactic polypropylene.

4. The compound of claim 2, wherein the polypropylene is amorphous.

5. The compound of claim 2, wherein the polypropylene includes isotactic or syndiotactic crystallizable units.

6. The compound of claim 2, wherein the polypropylene includes meso diads constituting from about 30% to about 99.5% of the total diads of the polypropylene.

7. The compound of claim 2, wherein at least one of $R_1$, $R_{71}$, and $R_{91}$ has a number-averaged molecular weight of from about 300 to about 30000 g/mol.

8. The compound of claim 2, wherein at least one of $R_1$, $R_{71}$, and $R_{91}$ has a number-averaged molecular weight of from about 500 to about 5000 g/mol.

9. The compound of claim 1, wherein at least one of $R_1$, $R_{71}$, and $R_{91}$ comprises polyethylene.

10. The compound of claim 1, wherein at least one of $R_1$, $R_{71}$, and $R_{91}$ comprises poly(ethylene-co-propylene).

11. The compound of claim 10, wherein at least one of $R_1$, $R_{71}$, and $R_{91}$ comprises from about 1 mole % to about 90 mole % of ethylene units and from about 99 mole % to about 10 mole % propylene units.

12. The compound of claim 11, wherein at least one of $R_1$, $R_{71}$, and $R_{91}$ comprises from about 10 mole % to about 50 mole % of ethylene units.

13. The compound of claim 1, wherein at least one of $R_1$, $R_{71}$, and $R_{91}$ comprises poly(higher alpha-olefin), the higher alpha-olefin including two or more carbon atoms on each side chain.

14. The compound of claim 1, wherein at least one of $R_1$, $R_{71}$, and $R_{91}$ comprises poly(propylene-co-higher alpha-olefin), the higher alpha-olefin including two or more carbon atoms on each side chain.

15. The compound of claim 1, wherein the nitrogen content in the compound is about 1 wt % to about 10 wt % based on the total weight of the compound.

16. The compound of claim 1, wherein $R_3$ is —CH$_2$—CH$_2$—, and $R_{31}$ is hydrogen.

17. The compound of claim 16, wherein the —N($R_{31}$)—$R_3$— repeat unit is interrupted in one or more places by a 1,4-diethylenediamine.

18. A compound produced by the method comprising:
(a) converting a polymer base unit $R_{11}$ which is a branched or straight-chained $C_{10}$-$C_{800}$ alkyl or alkenyl group having a vinyl terminal group, to a polymer having polyanhydride terminal group represented by:

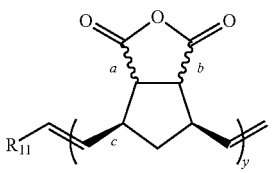

wherein y is an integer between 1 and 20 inclusive, a and b are C—C bonds in cis-configuration with respect to each other and in either cis- or trans-configuration with respect to bond c; and
(b) reacting the polymer obtained in (a) with a polyamine represented by

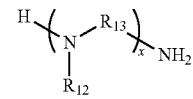

wherein $R_{12}$ is hydrogen or a $C_1$-$C_4$ branched or straight chained alkyl optionally substituted with one or more amine groups, $R_{13}$ is a $C_1$-$C_4$ branched or straight chained alkylene group, and x is an integer between 1 and 10, and further wherein the —N($R_{12}$)—$R_{13}$— unit is optionally interrupted in one or more places by a nitrogen-containing heterocyclic cycloalkyl group, and wherein when the x-th —N($R_{12}$)—$R_{13}$— unit along with the terminal nitrogen atom forms a heterocyclic cycloalkyl group, the terminal —NH$_2$ is replaced by a —NH— group for valency.

19. The compound of claim 18, wherein $R_{11}$ comprises polypropylene.

20. The compound of claim 19, wherein the polypropylene is atactic polypropylene, isotactic polypropylene, or syndiotactic polypropylene.

21. The compound of claim 19, wherein the polypropylene is amorphous.

22. The compound of claim 19, wherein the polypropylene includes isotactic or syndiotactic crystallizable units.

23. The compound of claim 19, wherein the polypropylene includes meso diads constituting from about 30% to about 99.5% of the total diads of the polypropylene.

24. The compound of claim 18, wherein the molar ratio of $R_{11}$ polyamine is between about 5:1 and about 1:5.

25. The compound of claim 18, wherein $R_{11}$ has a number-averaged molecular weight of from about 300 to about 30000 g/mol.

26. The compound of claim 25, wherein $R_{11}$ has a number-averaged molecular weight of from about 500 to about 5000 g/mol.

27. The compound of claim 18, wherein $R_{11}$ comprises polyethylene.

28. The compound of claim 18, wherein $R_{11}$ comprises poly(ethylene-co-propylene).

29. The compound of claim 18, wherein $R_{11}$ comprises from about 10 mole % to about 90 mole % of ethylene units and from about 90 mole % to about 10 mole % propylene units.

30. The compound of claim 29, wherein $R_{11}$ comprises from about 20 mole % to about 50 mole % of ethylene units.

31. The compound of claim 18, wherein $R_{11}$ comprises poly(higher alpha-olefin), the higher alpha-olefin including two or more carbon atoms on each side chain.

32. The compound of claim 18, wherein $R_{11}$ comprises poly(propylene-co-higher alpha-olefin), the higher alpha-olefin including two or more carbon atoms on each side chain.

33. The compound of claim 18, wherein $R_{11}$ comprises poly(ethylene-co-higher alpha-olefin), the higher alpha-olefin including two or more carbon atoms on each side chain.

34. The compound of claim 18, wherein at least 50% of the terminal vinyl groups of $R_{11}$ are an allylic vinyl group.

35. The compound of claim 18, wherein the polyamine comprise linear, branched or cyclic isomers of an oligomer of ethyleneamine, or mixtures thereof, wherein each two neighboring nitrogens in the oligomer of ethyleneamine are bridged by one or two ethyleneamine groups.

36. The compound of claim 35, wherein the polyamine is selected from ethylenediamine, diethylenetriamine, triethylenetetramine, tetraethylenepentamine, pentaethylenehexamine, hexaethyleneheptamine, and mixtures thereof.

37. The compound of claim 35, wherein the polyamine comprises a heavy polyamine.

38. The compound of claim 18, wherein (a) comprises reacting the polymer having the terminal vinyl group with norbornene-exo-2,3-dicarboxylic anhydride.

39. The compound of claim 18, wherein (a) comprises reacting the polymer having the terminal vinyl group with norbornene-endo-2,3-dicarboxylic anhydride.

40. The compound of claim 18, wherein the reaction in (a) is a ring opening cross metathesis reaction catalyzed by a tungsten or ruthenium metal complex-based metathesis catalyst.

\* \* \* \* \*